United States Patent
Ranta et al.

(10) Patent No.: US 8,084,752 B2
(45) Date of Patent: Dec. 27, 2011

(54) ULTRAVIOLET TREATMENT DEVICE

(75) Inventors: Craig Ranta, Redmond, WA (US);
Steven Fisher, Edmonds, WA (US)

(73) Assignee: VioGuard Corporation, Bothell, WA (US)

( * ) Notice: Subject to any disclaimer, the term of this patent is extended or adjusted under 35 U.S.C. 154(b) by 190 days.

(21) Appl. No.: 12/397,135

(22) Filed: Mar. 3, 2009

(65) Prior Publication Data

US 2009/0218512 A1    Sep. 3, 2009

Related U.S. Application Data (60) Provisional application No. 61/033,270, filed on Mar. 3, 2008, provisional application No. 61/098,510, filed on Sep. 19, 2008.

(51) Int. Cl.
*G01N 23/00* (2006.01)
(52) U.S. Cl. .................. 250/455.11; 250/504 R; 422/24
(58) Field of Classification Search .............. 250/455.11
See application file for complete search history.

(56) References Cited

U.S. PATENT DOCUMENTS

| | | | |
|---|---|---|---|
| 2,090,973 A | 8/1937 | Basham | |
| 2,254,977 A | 9/1941 | Prang | |
| 2,359,477 A | 10/1944 | Hoern | |
| 2,365,306 A | 12/1944 | Swebilius | |
| 2,400,389 A | 5/1946 | Cavallilto | |
| 4,975,587 A | 12/1990 | Min-Jenn | |
| 5,225,172 A | 7/1993 | Meyler et al. | |
| 5,288,647 A | 2/1994 | Zimlich, Jr. et al. | |
| 5,514,871 A | 5/1996 | Hayes et al. | |
| 6,278,122 B1 * | 8/2001 | Gagnon | 250/455.11 |
| 6,458,331 B1 * | 10/2002 | Roberts | 422/186.3 |
| 6,592,816 B1 * | 7/2003 | Ebel et al. | 422/62 |
| 6,720,950 B2 | 4/2004 | Cheng | |
| 7,068,361 B2 * | 6/2006 | Cimino et al. | 356/213 |
| 7,372,044 B2 | 5/2008 | Ross | |
| 7,692,159 B2 * | 4/2010 | Lane et al. | 250/455.11 |
| 2004/0046795 A1 | 3/2004 | Josephson et al. | |
| 2006/0186358 A1 | 8/2006 | Couvillion | |

FOREIGN PATENT DOCUMENTS

| | | |
|---|---|---|
| CN | 201184995 | 1/2009 |
| CN | 101393468 | 3/2009 |
| CN | 201223570 | 4/2009 |
| GB | 2387530 | 10/2003 |
| GB | 2421220 | 6/2006 |
| GB | 2422807 | 8/2006 |
| GB | 2424971 | 10/2006 |
| GB | 2446387 | 8/2008 |
| JP | 7160362 | 6/1995 |
| WO | 2008096123 | 8/2008 |

* cited by examiner

*Primary Examiner* — Phillip A Johnston
(74) *Attorney, Agent, or Firm* — Lowe Graham Jones PLLC (57) ABSTRACT

A keyboard and touchpad or mouse UV treatment system with optical sensor and inclined slide is described. A proximity sensor, microcontroller firmware, and motorized mechanism allow activation of the sanitization cycle by personnel with contaminated hands without risk of additional spreading of pathogens to other personnel and patients. The inclined slide provides stability when operated on a desk, and the microcontroller and optical sensor determine the proper exposure time to compensate for lamp aging and variations in lamp output.

23 Claims, 6 Drawing Sheets

External view of preferred embodiment when open

Figure 1
External view of preferred embodiment when open

Figure 2
External view of preferred embodiment when closed

Figure 3
Cutaway side view of preferred embodiment when slide extended

Figure 4
Block diagram of preferred embodiment

Bacteria

| | 90% kill energy (uW/cm²-sec) | 100% kill energy |
|---|---|---|
| Bacillus anthracis - Anthrax | 4,520 | 8,700 |
| Bacillus anthracis spores - Anthrax spores | 24,320 | 46,200 |
| Bacillus magaterium sp. (spores) | 2,730 | 5,200 |
| Bacillus magaterium sp. (veg.) | 1,300 | 2,500 |
| Bacillus paratyphusus | 3,200 | 6,100 |
| Bacillus subtilis spores | 11,600 | 22,000 |
| Bacillus subtilis | 5,800 | 11,000 |
| Clostridium tetani | 13,000 | 22,000 |
| Corynebacterium diphtheriae | 3,370 | 6,510 |
| Ebertelia typhosa | 2,140 | 4,100 |
| Escherichia coli | 3,000 | 6,600 |
| Leptospiracanicola - infectious Jaundice | 3,150 | 6,000 |
| Microccocus candidus | 6,050 | 12,300 |
| Microccocus sphaeroides | 1,000 | 15,400 |
| Mycobacterium tuberculosis | 6,200 | 10,000 |
| Neisseria catarrhalis | 4,400 | 8,500 |
| Phytomonas tumefaciens | 4,400 | 8,000 |
| Proteus vulgaris | 3,000 | 6,600 |
| Pseudomonas aeruginosa | 5,500 | 10,500 |
| Pseudomonas fluorescens | 3,500 | 6,600 |
| Salmonella enteritidis | 4,000 | 7,600 |
| Salmonela paratyphi - Enteric fever | 3,200 | 6,100 |
| Salmonella typhosa - Typhoid fever | 2,150 | 4,100 |
| Salmonella typhimurium | 8,000 | 15,200 |
| Sarcina lutea | 19,700 | 26,400 |
| Serratia marcescens | 2,420 | 6,160 |
| Shigella dyseteriae - Dysentery | 2,200 | 4,200 |
| Shigella flexneri - Dysentery | 1,700 | 3,400 |
| Shigella paradysenteriae | 1,680 | 3,400 |
| Spirillum rubrum | 4,400 | 6,160 |
| Staphylococcus albus | 1,840 | 5,720 |
| Staphylococcus aerius | 2,600 | 6,600 |
| Staphylococcus hemolyticus | 2,160 | 5,500 |
| Staphylococcus lactis | 6,150 | 8,800 |
| Streptococcus viridans | 2,000 | 3,800 |
| Vibrio comma - Cholera | 3,375 | 6,500 |

Figure 6B

| Molds | 90% kill energy | 90% kill energy |
|---|---|---|
| Aspergillius flavus | 60,000 | 99,000 |
| Aspergillius glaucus | 44,000 | 88,000 |
| Aspergillius niger | 132,000 | 330,000 |
| Mucor racemosus A | 17,000 | 35,200 |
| Mucor racemosus B | 17,000 | 35,200 |
| Oospora lactis | 5,000 | 11,000 |
| Penicillium expansum | 13,000 | 22,000 |
| Penicillium roqueforti | 13,000 | 26,400 |
| Penicillium digitatum | 44,000 | 88,000 |
| Rhisopus nigricans | 111,000 | 220,000 |
| | | |
| Protozoa | | |
| Chlorella Vulgaris | 13,000 | 22,000 |
| Nematode Eggs | 45,000 | 92,000 |
| Paramecium | 11,000 | 20,000 |
| | | |
| Virus | | |
| Bacteriopfage - E. Coli | 2,600 | 6,600 |
| Infectious Hepatitis | 5,800 | 8,000 |
| Influenza | 3,400 | 6,600 |
| Poliovirus - Poliomyelitis | 3,150 | 6,600 |
| Tobacco mosaic | 240,000 | 440,000 |
| | | |
| Yeast | | |
| Brewers yeast | 3,300 | 6,600 |
| Common yeast cake | 6,000 | 13,200 |
| Saccharomyces carevisiae | 6,000 | 13,200 |
| Saccharomyces ellipsoideus | 6,000 | 13,200 |
| Saccharomyces spores | 8,000 | 17,600 | ced
ULTRAVIOLET TREATMENT DEVICE

PRIORITY CLAIM

This invention claims the benefit of prior provisional application Ser. No. 61/033,270 filed on Mar. 3, 2008 and provisional application Ser. No. 61/098,510 filed on Sep. 19, 2008.

BACKGROUND OF THE INVENTION

With increasing numbers of hospitals, clinics, and dental offices moving to fully computerized patient record systems, the number of computer keyboards and mice in these facilities has been steadily increasing. Keyboards and mice contaminated with pathogens have been identified as one of the leading vectors for transmission of infections and viruses from patient to patient in hospitals and clinics. Healthcare acquired infections such as MRSA (Methicillin Resistant *Staphylococcus Aureus*) cause tens of thousands of deaths each year in the US alone, cost the economy billions through extended hospital stays and wrongful death lawsuits, and contribute to rising medical costs worldwide. A significant percentage of patient to patient transmission of pathogens can be eliminated if there is an effective and simple way to sanitize computer keyboards and mice after each use.

Hand washing policies and regular keyboard cleaning policies have had limited effectiveness in practice since they must take place before every use to eliminate any possibility of patient to patient contamination through the hands of a healthcare worker. Large medical facilities with hundreds or thousands of computer keyboards and mice have deemed it impractical to manually sanitize them with disinfectant more than once or twice per day, even though they may be used by dozens of contaminated employees in between cleanings.

Beyond the hospital setting, there are several other environments in which keyboards or other such equipment are shared by multiple users, thereby facilitating the transfer of germs from one person to another. One such example includes keyboards and mice for computers in typical public libraries.

Germicidal short wave ultraviolet light at 253.7 nm is known as an effective, rapid way to sanitize non-porous, flat surfaces. The germ killing effectiveness of such lamps is a function of total UV energy exposure which is the mathematical product of intensity (power per unit area) and time. Lamps which generate this wavelength are readily available commercially. However, the output of commonly available UV lamps drops significantly over time, and is also affected by voltage, current, manufacturing differences between lamps, and accumulation of dust and other contaminants on the bulb.

Others have tried to construct UV sanitation enclosures, with limited success. U.S. Pat. No. 6,278,122 by Gagnon describes a UV sanitization enclosure for a mouse and keyboard with a sliding drawer mechanism in which a front door hinged at the bottom doubles as a palm rest. U.S. Pat. No. 6,458,331 by Roberts eliminates the drawer mechanism and describes a simple box with a switch which is placed over a mouse and keyboard to be sterilized. U.S. Pat. No. 7,372,044 by Ross describes various configurations of a sanitization box housing various input devices with a window which blocks UV and passes visible light. Each of these devices includes one or more of the shortcomings listed above, or has yet other problems.

SUMMARY OF THE INVENTION

A preferred version of the invention consists of a substantially light tight box with an inclined motorized drawer and door that opens to allow use of the integral touchpad and keyboard, and which closes to form an ultraviolet light-tight enclosure during which a rapid sanitizing cycle can be performed. The mechanism and internal germicidal lamp is preferably activated without touching the device by means of an infrared proximity sensor similar to those used in touchless faucets and towel dispensers commonly seen in public restrooms.

In some preferred versions of the invention, the sanitizing cycle can be manually activated by waving a hand near the sensor. In other versions, it may be activated by touching a special key on the keyboard, or automatically activated after a programmable period of inactivity of the touchpad and keyboard. In yet other examples, the device can be controlled programmatically by an attached PC and control software.

In one example of the invention, the sanitizer includes a controller and light sensor which measures the intensity of light emitted by the UV source in one or more spectral ranges, and determines the duration of the exposure required to achieve a target total UV energy dosage. Alternatively, the UV light may be collected and emitted as visible light, with an accompanying visible light sensor provided to measure visible light exposure as a proxy for UV light exposure.

In some versions, an inclined slide allows a front edge of the slide to contact the desktop surface at full extension, providing mechanical stability during use.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

One example of the invention includes a method to determine total required exposure time by either directly measuring the UV-C output at 253.7 nm or indirectly by measuring the intensity of one or more spurious spectral lines of the lamp in the visible region of approximately 380-750 nm as a proxy for the UV lamp output, and then calculating the exposure duration and terminating the exposure when the desired total energy has been reached. Direct measurement of the UV-C light can be accomplished with a sensor such as a silicon-carbide photodiode. However, such devices are expensive and so not desirable for inclusion in a high volume production device.

In the case of indirect measurement of UV emissions, a low cost visible or even wide spectrum infrared sensor can be used. The relative amplitudes of spurious visible spectral lines emitted by a UV source and their ratio to the primary UV output can be determined in advance for a particular source. Thus, knowledge of the lamp aging characteristics and measurement of the spurious spectral lines can be used to compute the estimated lamp output in a more cost effective way than direct UV measurement. A broad spectrum sensor can also double as a chassis intrusion detector, allowing the UV source to operate only when there is no detected visible light before turning the UV source on. A chassis intrusion detector prevents the sanitizer unit from being operated when the enclosure has been opened in a lighted room to avoid potentially hazardous UV exposure to service personnel. This would normally be used as an adjunct safety measure to a regular interlock switch.

In yet other versions of the invention, as discussed in greater detail below, UV light may be converted to visible light in order to measure the converted visible light as another method for indirect measurement of UV exposure. For example, one or more locations within the device may include a phosphorescent region which will illuminate in the visible spectrum in response to being subjected to UV light. A sensor positioned to detect the visible light cast by the phosphor can then be used to indirectly measure UV exposure.

While some forms of the current invention may be used with computer systems having a mouse-based input system, a computer mouse is particularly difficult to disinfect since it has sloping sides, an accessible bottom, and usually a cable. This shape creates shadows and resulting non-uniform UV light distribution which prevents UV disinfection from a non-diffuse source from operating effectively. One version of this invention replaces the mouse with an integral touchpad and control buttons which do not create shadowing and are easily sanitized by UV light.

Prior devices also either do not address, or address incompletely, the problem of opening and closing the sanitizer with contaminated hands. Manual opening and closing of the sanitizing drawer with a handle or knob or automatic opening and closing by pressing a button simply moves the potential point of cross contamination to the handle, knob, or button. A preferred version of the invention avoids the cross-contamination problem of operating the drawer by using a touchless proximity sensor to open the sanitizing drawer and a button located on the inside of the drawer to close the drawer. In this manner the close button, which activates an automated closure of the sanitizing drawer, is sanitized immediately after being touched. Similarly, while the drawer is open and the input device is being used, the proximity sensor can be disabled to prevent inadvertent activation while there is hand movement on and near the keyboard and touchpad. This combination of proximity sensing and automatic closure using an inside button improves the usability and effectiveness over that of prior devices.

Prior devices which incorporate sliding drawer mechanisms also fail to address usability issues relating to stability of the device on a desk when the drawer slide is extended. When a user rests their hands on a keyboard which is sitting on an extended drawer slide, the entire enclosure can become unstable and rock forward. One version of the current invention inclines the slide at an angle which causes the outermost portion of the slide to rest on the work surface at full extension, creating a stable surface on which to rest arms and wrists. This preferred version includes a motorized drawer slide mechanism having an integral keyboard and touchpad. Note that while the preferred implementation is described as having a sliding drawer, such a version should be understood to include telescoping, scissor, or other mechanical means for enabling the drawer to laterally deploy and retract within a housing.

The preferred embodiment of the present invention performs sanitization by utilizing UVC, short wave ultraviolet radiation in the wavelength region of 100-280 nm, which is produced by commercially available fluorescent lamps sold for germicidal purposes.

Referring the Figures generally, a preferred version of the invention is described. As shown, the device includes a housing having a motorized sliding drawer 107. The drawer my comprise a generally flat shelf, and is configured to allow the drawer to deploy externally to the housing and to retract within the housing. The drawer may be secured to the housing via sliding rails, telescoping extensions, scissor connections, or other means. A keyboard 104 rests on the drawer, though in some configurations the lower surface of the keyboard itself serves as the drawer. The keyboard may include a touchpad 103 and a sanitizer button 104. At an external location on the housing a proximity sensor 101 and status light 106 are provided.

After a user completes a computer session that uses the keyboard or touchpad resting on the sanitizer drawer, the infrared treatment may be initiated in any of several ways. In one version, treatment is triggered by a treatment button that may be provided either on the keyboard itself, on the sliding drawer, or at another location on the housing. In the case of a button on the housing or drawer, the button may be connected to the microcontroller which initiates the treatment cycle. Alternatively, and preferably with respect to a button or key located on the keyboard, the associated personal computer may have a corresponding program that detects when the button or key is pressed and then, in communication with the microcontroller, initiates the treatment cycle.

The inclusion of a subroutine operable by the personal computer in connection with the ultraviolet treatment device allows for an additional treatment trigger related to a period of inactivity of the keyboard, touchpad, or mouse. In this implementation, the personal computer monitors keyboard activity, measuring periods of inactivity. After a specified period of inactivity, the personal computer automatically triggers the retraction of the drawer and the initiation of the treatment cycle. The period of inactivity that results in the cleaning cycle may be preset or adjusted by the user. For example, the time period may be 10 minutes, 30 minutes, or any other desired time.

Figure 1:
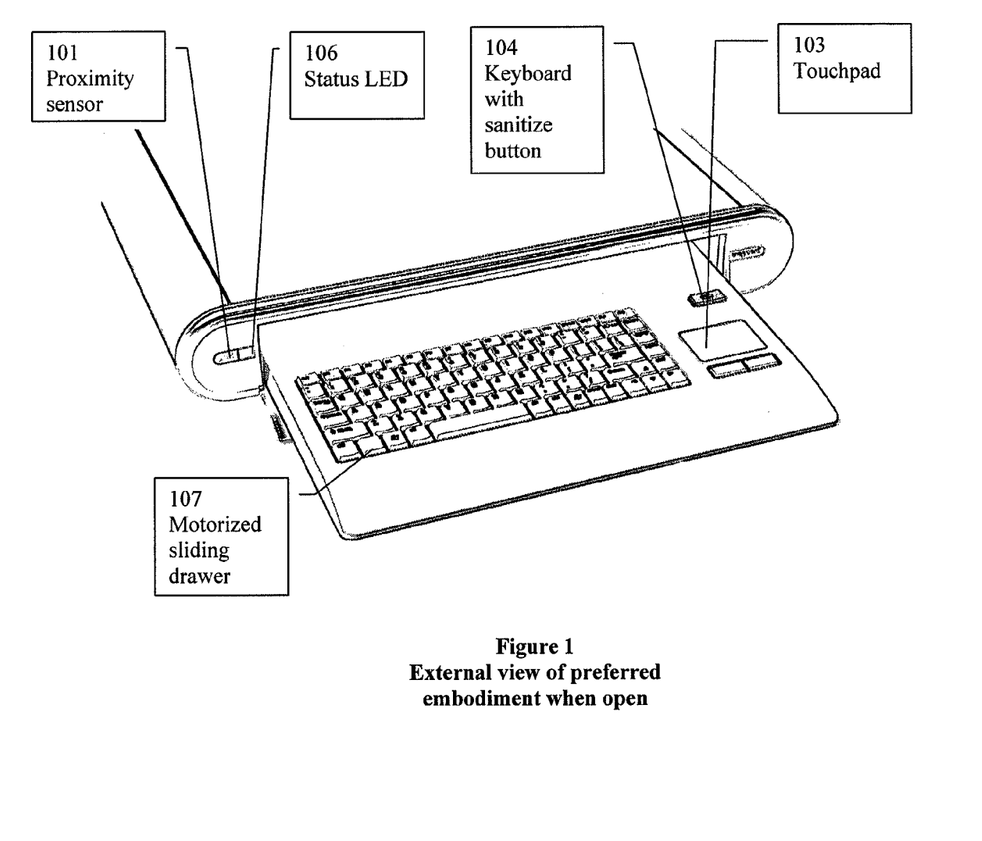
FIG. 1 is an external view of one possible embodiment of the automatic keyboard and touchpad sanitizer with externally visible features and controls. In this view the drawer slide is open.
Figure 2:
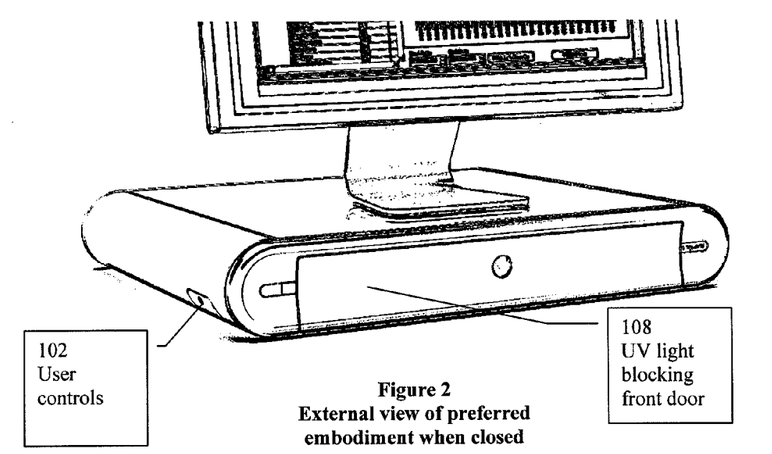
FIG. 2 is an external view of one possible embodiment of the automatic keyboard and touchpad sanitizer. In this view the drawer slide is closed.
Figure 3:
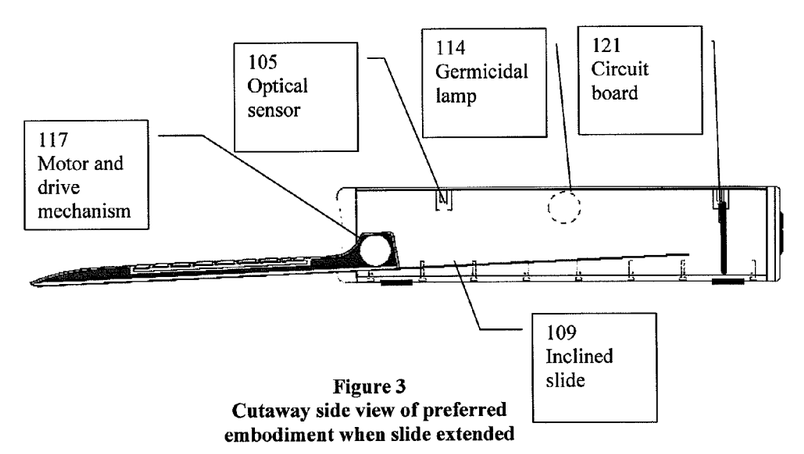
FIG. 3 is a cutaway side view of the automatic sanitizer showing the inclined slide, optical sensor, UV lamp, motor and drive mechanism, and the circuit board.
Figure 4:
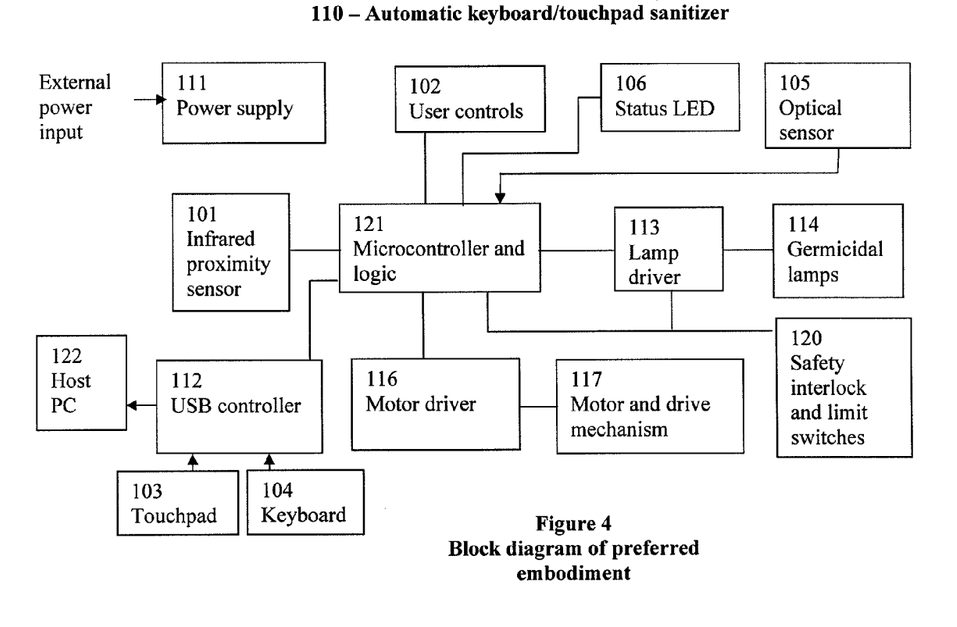
FIG. 4 is a block diagram of the electromechanical elements of the invention.

Other versions may include a touchless sensor mounted on the device at any location, including for example on the housing, on the drawer, or on the keyboard. In one such example, the user waves a hand near the infrared sensor 101 to begin a sanitization cycle. As shown in FIG. 3, the proximity sensor is in communication with a microprocessor and memory having stored programming instructions (or logic) 121. Upon sensing an appropriate reflection of light corresponding to a distance from a hand or other object in relation to the sensor, the drawer will retract and a sanitizing routine will begin. In the version as shown, the sensor is illustrated as being on a front face of the housing, facing toward the location where a user would sit when using the keyboard. In other versions, the sensor may be positioned on a side or on top of the housing.

Alternatively, after a period of inactivity detected by microcontroller 121, a cycle may begin automatically, in accordance with stored programming logic. The mode of operation is set by the user with controls 102 or alternatively with a software application running on the PC. User controls 102 are preferably hidden behind an access door to prevent inadvertent changes in settings.

Upon initiation of the cleaning cycle, the motorized drawer 105 retracts and a front door 108 closes, forming a light tight box. Once the door is closed, the microprocessor causes the illumination of a germicidal lamp 113. During the sanitization cycle, the status indicator 106 is illuminated to show that a cycle is in process. A cycle may take from a few seconds to several minutes, depending on inputs from user controls 102. In one version, a standard default cycle length is provided in the control logic, with the default cycle length being set to a dosage that is great enough to sanitize germs most likely to be present on the keyboard. As noted above, the dosage is preferably measured in terms of actual UV light emitted, as opposed to a duration of time based on a nominal lamp output. When the cycle is complete, status indicators 106 will indicate the sanitization is complete and the motorized drawer mechanism will remain retracted in its enclosure until commanded to extend by the next user.

A proximity sensor circuit 101 senses reflected infrared energy in the 840 nm range by transmitting infrared pulses at a known carrier frequency. A receiver circuit, sensitive only to the transmitted carrier frequency, receives the transmitted frequency when an object which scatters 840 nm energy approaches the transmitter. A digital signal is then sent to the microcontroller when a predetermined threshold is exceeded. The sensitivity threshold of the circuit is adjusted by design to trigger when a human hand approaches within a few cm, much like a touchless bathroom faucet or paper towel dispenser. The sensor is located to avoid accidental actuation and minimize direct illumination by the sun or overhead lights, which may reduce sensitivity. As noted above, the sensor is shown on an exemplary embodiment as being on a front face of the housing, but may be located on a side, on top, or in other positions.

User controls 102 may select a variety of disinfection times in order to target various pathogens, some of which require larger doses of UVC energy at 253.7 nm. This would likely be set by the policy of the facility and not adjusted by individual users. In other instances the disinfection times may be adjusted, as desired.

Microcontroller 121 and contained firmware or other memory storage devices implement all the timing, logic, and controls necessary for operation of the sanitization device. Advanced functions such as a more thorough and lengthy sanitization which takes place during low usage hours can be implemented in cooperation with the host PC 122 utilizing the USB port for bidirectional communication.

USB controller 112 serves two functions; it combines two USB signals from the touchpad and keyboard into a single USB host connection, and provides a port for microcontroller 121 to monitor touchpad and keyboard activity for purposes of idle detection in automatic mode. The memory associated with the microcontroller 121 may be programmed to monitor for touchpad and keyboard packets on the USB interface as a proxy for system activity, and begin a sterilization cycle after a user selectable period of inactivity through user controls 102. Microcontroller 121 may optionally send and receive data to the PC host by enumerating as a separate USB device, allowing software control of the sanitizer parameters, and enabling advanced features such as time of day based sanitization cycles. In an alternate low cost embodiment, microcontroller 121 and USB controller 112 may be combined into a single controller.

A safety interlock circuit 120 consists of one or more optical or mechanical switches which indicate to the microcontroller 121 that the door is fully closed. In addition, the safety interlock circuit 120 supplies power to the lamp driver 113 only when the door is fully closed, providing protection against failure of the microcontroller 121.

The lamp driver 113 in the preferred embodiment is a rapid start or programmed start fluorescent lamp circuit which provides the proper starting voltage and current necessary to start and operate one or more germicidal fluorescent lamps 114 for a large number of off/on cycles. One or more commonly available germicidal lamps, such as a G25T8, a 25 watt UVC lamp, is used as the germicidal source, positioned as close to the keyboard and touchpad as practical, and used in conjunction with UV reflective material on the inside of the enclosure to improve the distribution and uniformity of the UVC light.

Previous devices contemplate termination of a treatment cycle when a predetermined time period has expired. However, since the UV output of the lamps diminishes over time, diminishes with dust and dirt accumulation on the UV lamps, and varies with differences in voltage and current from the lamp power supply, terminating the disinfection cycle after a predetermined time interval may not always deliver the correct kill dosage to the item being treated. Furthermore, differences in lamp construction, impedance, and output characteristics between manufacturers create further opportunities for errors in applying the correct dosage of ultraviolet light. A better way to terminate the cycle is to measure the UVC output directly or indirectly (as explained in #1 above), mathematically integrating the output over time so as to calculate total dosage, then terminating the treatment cycle when the correct total dosage is reached. In this manner, better exposure control is achieved and more reliable treatment.

An optical sensor 105 connects to the microcontroller 121 and allows it to measure the intensity of the UVC light from germicidal lamps 114 directly. In alternate versions the optical sensor may include a low cost visible spectrum sensor, either separately or in addition to the sensor for measuring UVC intensity, to measure spurious spectral lines from the lamps as a proxy for the main germicidal output. The intensity is measured by the microcontroller and the exposure duration is calculated for every sanitization cycle and controlled by microcontroller 121.

In alternate versions of the invention, UV energy is sensed and measured using a UV-excitable phosphor which re-radiates visible light and a visible light sensor. Ideally, the best implementations of the invention will be able to detect the intensity of UVC light in order to determine whether the UVC light source is functioning properly and in the range of its normal output. Disinfection will not occur properly unless the proper dosage is achieved, where dosage is a function of the light intensity and the time or duration of the light. If intensity is a constant then the dosage can be determined solely as a function of time. However, UVC light sources may have a somewhat inconsistent intensity, and further tend to decrease their intensity over time, so it is desirable to be able to measure dosage as a function of intensity, and also to be able to inform the user when the light source requires replacement because intensity has fallen below its rated output. In the case of multiple light sources, detection of the UVC output can determine if each of the sources is functioning properly and also inform the user via an indicator whether the sources need replacement.

Some examples of the present invention use a low cost visible light detector as a means for detecting UVC energy by converting the UVC energy to visible light energy with a phosphor. There are a wide variety of phosphor powders available commercially which will convert light energy of one wavelength to light of another wavelength, typically a longer wavelength, with some fixed conversion efficiency. This is precisely how commercial fluorescent lamps work; they generate UV energy from an ionized gas in a glass tube, and the inside of the glass tube is coated with a phosphor which glows white when illuminated by UV light. Such a powder can be mixed in a certain ratio with an optically clear moldable material such as silicone rubber, molded into the desired shape such as a cylindrical cap, then applied over the top of the visible light detector.

Figure 5A:
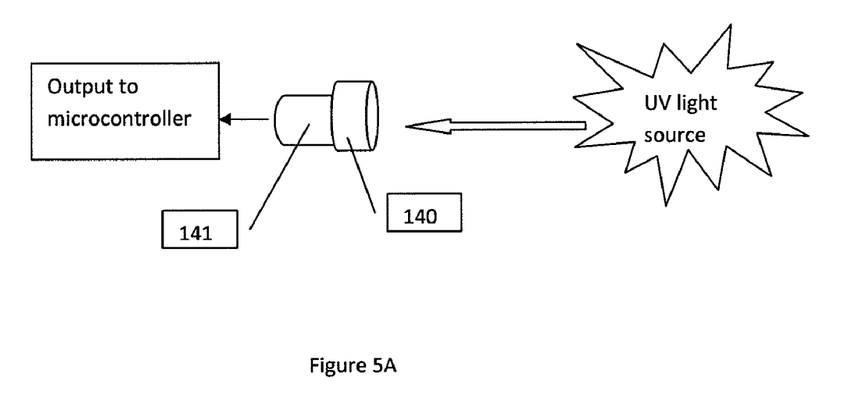
FIGS. 5A and 5B are representative views of a visible light sensor as incorporated into certain versions of the invention.

An example of this implementation is shown in FIG. 5A. Light from a UV light source illuminates a cap 140 of the type described above in which phosphor is integrated into a clear material such as silicone rubber. The cap 140 is provided over the receiving surface of a sensor 141 such that visible light originating from the phosphor within the cap is received by the sensor. The output from the sensor is coupled to the microcontroller so that stored programming logic can measure the UV dosage as a function of the intensity of the received visible light over time.

Figure 5B:
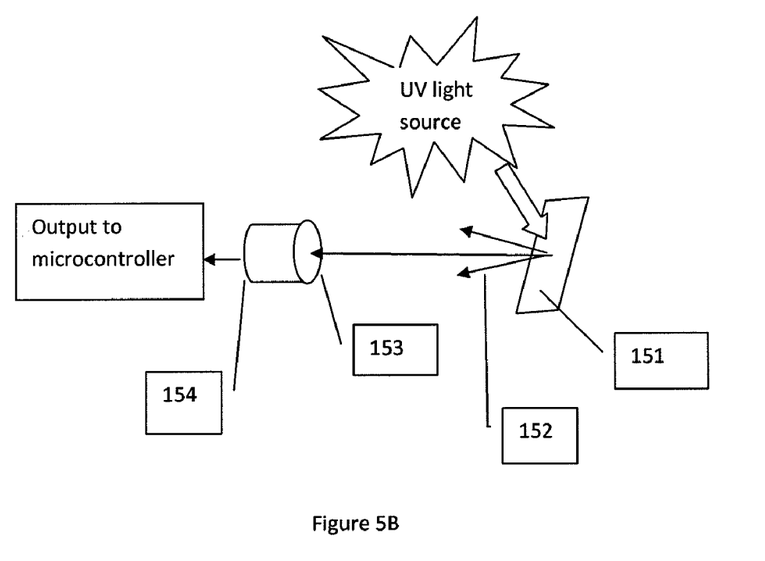

In another version, shown in FIG. 5B, the phosphor may be mixed with a suitable paint and applied to a surface 151 near the detector. Alternatively, the phosphor may be applied directly and adhered to a surface near the detector. The detector or sensor 154 is pointed toward the phosphor painted surface or is equipped with a lens 153 that focuses on the phosphor painted surface, which will re-radiate visible light 152 when exposed to UVC light. The visible light detector will then output an electrical signal proportional to the incident intensity of UVC light, multiplied by the conversion efficiency of the phosphor.

In either version, the microcontroller operates programming instructions stored in the memory to determine when the desired dosage has been reached by combining the sensed intensity over the time duration of the operation of the light. When a desired dosage has been reached, the microcontroller can cause the light to shut off.

Dosage ranges for the UV disinfection cycles may be stored in a memory accessible by the microprocessor in order to ensure that the keyboard or other device has been properly disinfected. Various organisms which are susceptible to being destroyed by UVC light have wide variations in the dosages required to kill them. The dosage is simply the intensity in energy per unit area, typically microwatts per square centimeter ($\mu W/cm^2$), multiplied by the exposure time in seconds.

Figure 6A:
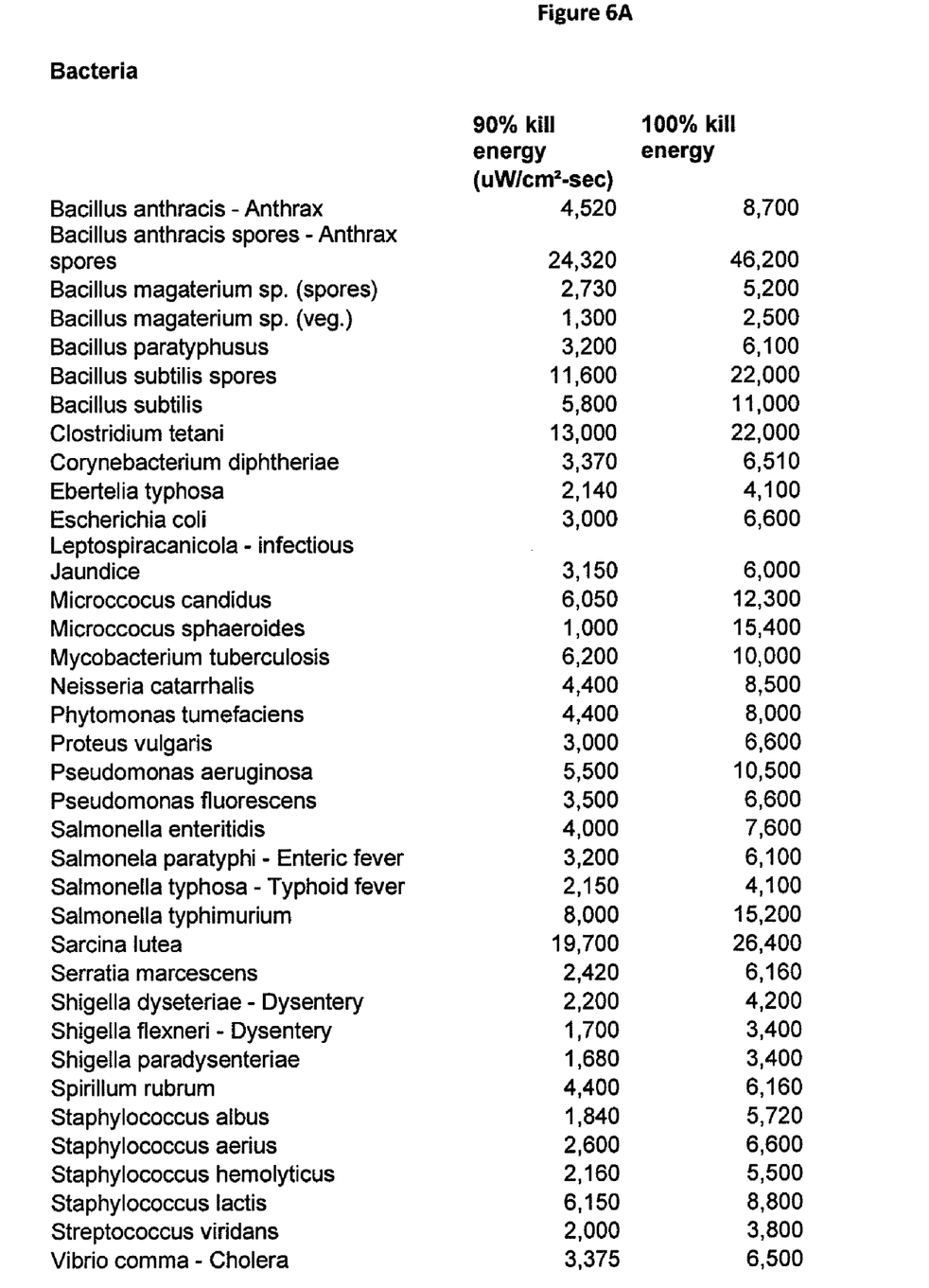
FIGS. 6A and 6B are tables providing preferred illumination dosages to kill selected pathogens.
Figure 6B:
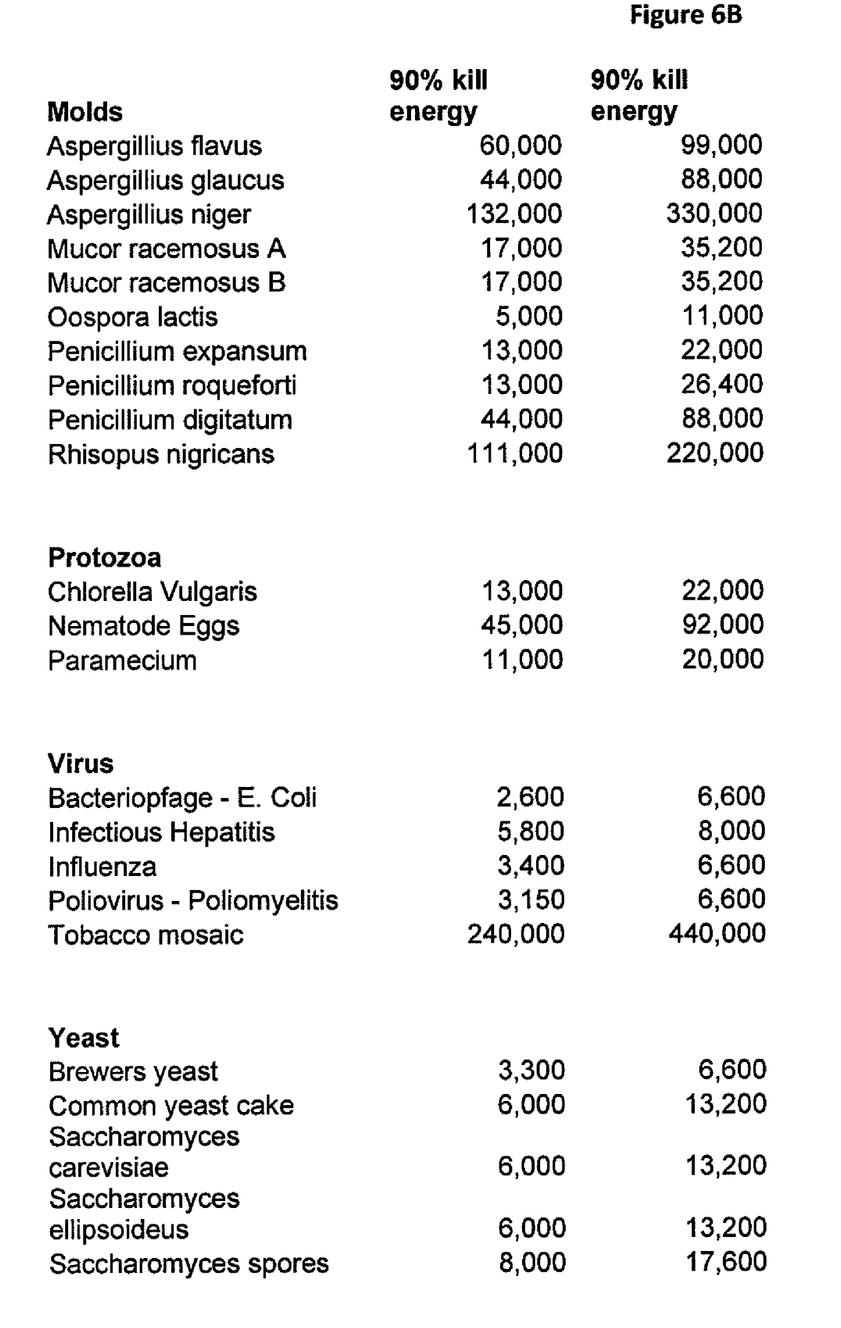

Example dosage ranges are provided in the tables of FIG. 6, and generally include dosages of between about 1000 microwatt-sec/square cm to 440,000 microwatt-sec/square cm. The dosage times are based on the use of a lamp producing about 800 microwatts/square cm. The actual intensity of a lamp may vary, however, making a time-based treatment system less desirable. Depending on the UV lamp output, the dosage durations would be changed accordingly. As an alternative, as discussed more fully below, a preferred system monitors UV exposure rather than time.

In a preferred implementation, the memory contains stored tables such as those of FIG. 6. In one such version, a user interface presented on the computer display allows a user to select a dosage based on particular pathogens. As noted above, the present UV device may be connected to the personal computer via a USB or other connection. In such a version, the computer may present the information from the tables of FIG. 6, allowing the user to select a dosage level corresponding to particular types of pathogens. In other versions, the user may select dosages based upon individual pathogens or groupings of them. Likewise, controls placed on the housing may simply incorporate switches or dials allowing the user to indicate desired dosages. Such selections may be configured to indicate particular pathogens, percentage levels, or in a high-medium-low configuration of options.

For example, the greatest dosage expected to be required for a 100 percent kill dosage for bacteria is approximately 46,000 microwatt-sec/square cm. The controls may provide for a "100 percent bacteria" setting, under which the device will operate for a sufficient duration (based upon the sensed intensity levels, as described above) to produce the desired dosage. The controls may also provide for a "90 percent bacteria" setting, in which the lamp operates for the duration sufficient to kill 90 percent of all bacteria. Other settings may be provided for molds, viruses, or other pathogens specifically, and may allow for either 100 percent kill dosages or a desired percentage other than 100 percent. An additional setting may indicate a dosage for all known pathogens, and another setting for high intensity disinfection in which the device operates for a duration beyond that which is believed to be a necessary dosage to kill all known pathogens. In one version, the device includes a default setting which will kill 100 percent of all bacteria. Termination of the disinfection cycle occurs when a total desired dosage is reached. It should be appreciated that an absolute 100% kill is statistically unlikely to be achieved with this type of device; instead microbiologists speak of a "log 4 reduction" or a "log 5 reduction", for example, which means 99.99% and 99.999% kill, respectively.

The operation of the drawer and door mechanisms are further described below with reference to the figures. A motor driver 106 converts signals from the microcontroller 121 to appropriate drive signals for a motor 117 to drive the drawer mechanism the appropriate direction and speed, and allows monitoring of motor current to check if the mechanism is blocked or jammed.

The motor and drive mechanism 117 in the preferred embodiment is a DC motor with a belt reduction and worm drive mechanism, but may also be a rack and pinion drive with DC stepper motor or take still other forms. The mechanism is designed so that it may be manually operated without damage, and any stopping or slowing of the mechanism during activation can be sensed by the microcontroller and will result in stopping or reversing the drawer mechanism so as to not pinch hands or objects in the drawer. If the drawer is manually forced open during a sanitization cycle, safety interlock circuit 120 will interrupt power to the sanitization lamps.

An inclined slide 109 is set at an angle which will allow the end of the slide to contact the surface on which the sanitizer is sitting (such as the top surface of a table or desk) when the slide is at full extension. This provides additional stability to prevent the enclosure from rocking when weight is applied to the keyboard wrist rest.

A power supply 111 converts AC power or external DC power to voltages needed by the internal circuitry.

The keyboard 104 and touchpad 103 are designed with materials that are resistant to degradation from exposure to ultraviolet light, features that minimize shadowing of the disinfecting light, and may also be of the sealed varieties that allow liquid disinfection to be used as part of a two-pronged infection control approach in especially sensitive areas such as surgical rooms.

Although the invention described within specifically includes a computer touchpad and keyboard, the automatic sanitization enclosure may be used or optimized for any type of object that may require sanitization.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims.

The embodiments of the invention in which an exclusive property or privilege is claimed are defined as follows:

1. A treatment device, comprising:
    a housing configured to retain ultraviolet light within an interior of the housing, the housing further having a door sized and configured to support a computer keyboard;
    an ultraviolet light positioned to illuminate the interior of the housing;
    a touchless sensor, the touchless sensor being coupled to the ultraviolet light to cause the light to illuminate when the touchless sensor senses a condition associated with an illumination mode of operation; and
    an illumination sensor causing the light to operate for a period of time sufficient to apply a desired dosage from the ultraviolet light, the desired dosage being a function of the intensity and duration of the light received by the sensor.

2. The treatment device of claim 1, wherein the touchless sensor is a motion detector.

3. The treatment device of claim 2, wherein the condition further comprises the presence of a motion of an object within a field of view of the motion detector.

4. The treatment device of claim 2, further comprising a drawer secured to the housing for movement between a retracted position within the housing and an extended position at least partially external to the housing.

5. The treatment device of claim 4, wherein the drawer has a front end and a back end, the front end extending external to the housing in the extended position, and further wherein the front end is inclined with respect to the back end in the extended position.

6. The treatment device of claim 5, further comprising a ramp within the housing, wherein the drawer is extendable along the ramp between the extended and retracted positions.

7. The treatment device of claim 2 wherein the housing has an external surface having a front external surface adjacent the door, further wherein the motion detector is positioned adjacent the door.

8. The treatment device of claim 2 further comprising a microprocessor, a memory accessible by the microprocessor, and a motor configured to automatically cause the drawer to move between the extended and retracted positions, the memory further containing programming instructions operable by the processor to cause the motor to retract the drawer and close the door in response to the condition associated with an illumination mode of operation.

9. The treatment device of claim 2, further comprising a sensor coupled to the microprocessor, wherein stored programming instructions cause the light to operate for a period of time sufficient to apply a desired dosage from the ultraviolet light, the desired dosage being a function of the intensity of the light received by the sensor over a period of time.

10. The treatment device of claim 9, wherein the sensor is an ultraviolet light sensor.

11. The treatment device of claim 9, wherein the sensor is a substantially full spectrum light sensor.

12. The treatment device of claim 9, wherein the sensor is a visible light sensor, and wherein the device further comprises a means for converting ultraviolet light to visible light, the visible light being within the field of view of the sensor.

13. The treatment device of claim 9, wherein the sensor is a visible light sensor, and wherein the device further includes a phosphor-based material within the housing, the phosphor-based material being placed within a field of view of the sensor.

14. The treatment device of claim 13, wherein the phosphor-based material comprises a transparent cap having phosphor embedded within it, the cap being secured over the sensor.

15. The treatment device of claim 13, wherein the phosphor-based material comprises a paint having phosphor within it, the paint being applied to a surface within the housing, the painted surface being within a field of view of the sensor.

16. A treatment device, comprising:
    a housing configured to retain ultraviolet light within an interior of the housing and to receive within the interior of the housing at least one of a keyboard, a touchpad, or a mouse, the housing further having a door;
    an ultraviolet light positioned to illuminate the interior of the housing;
    a sensor configured to detect light illuminated within the housing;
    a memory; and
    a microprocessor in communication with the memory and the sensor, the microprocessor having stored programming instructions to cause the ultraviolet light to operate to apply a desired dosage from the ultraviolet light to illuminate the at least one of a keyboard, a touchpad, or a mouse, the desired dosage being a function of the intensity of the light received by the sensor.

17. The treatment device of claim 16, further comprising a touchless sensor, the touchless sensor being coupled to the microprocessor to cause the ultraviolet light to illuminate when the touchless sensor senses a condition associated with an illumination mode of operation.

18. The treatment device of claim 16, further comprising a retractable support for holding a keyboard, the retractable support being movable between an extended position outside the housing and a retracted position within the housing, the keyboard further being in communication with a computer, the computer being configured to operate programming instructions to enable the computer to determine a period of inactivity of the keyboard, the computer further being in communication with the microprocessor of the treatment device to cause the treatment device to begin an operation of the ultraviolet light in response to the period of inactivity.

19. The treatment device of claim 17, wherein the desired dosage is in the range of about 1000 microwatt-sec/square cm to about 440,000 microwatt-sec/square cm.

20. The treatment device of claim 17, further comprising a range of possible dosages stored in the memory, and a user interface whereby a user can select one of the range of possible dosages.

21. The treatment device of claim 20, wherein the range of specified dosages further comprises a plurality of expected kill percentages for one or more classes of pathogens.

22. The treatment device of claim 16, further comprising a retractable support for holding the at least one of a keyboard, a touchpad, or a mouse, the retractable support being movable between an extended position outside the housing and a retracted position within the housing, the keyboard, the touchpad, or the mouse further being in communication with a computer, the computer being configured to operate programming instructions to enable the computer to determine a period of inactivity of the keyboard, the touchpad, or the mouse, the computer further being in communication with the treatment device to cause the treatment device to begin an operation of the ultraviolet light in response to the period of inactivity.

23. The treatment device of claim 22, wherein the microprocessor and the memory are contained within the computer.

* * * * *